US00PP25174P3

(12) United States Plant Patent
Schoone

(10) Patent No.: US PP25,174 P3
(45) Date of Patent: Dec. 16, 2014

(54) ***PHALAENOPSIS* ORCHID PLANT NAMED 'DEEP LAKE'**

(50) Latin Name: *Phalaenopsis* hybrid
Varietal Denomination: Deep Lake

(71) Applicant: Floricultura, Heemskerk (NL)

(72) Inventor: René Schoone, Assendelft (NL)

(73) Assignee: Florocultura, Heemskerk (NL)

( * ) Notice: Subject to any disclaimer, the term of this patent is extended or adjusted under 35 U.S.C. 154(b) by 113 days.

(21) Appl. No.: 13/573,559

(22) Filed: Sep. 25, 2012

(65) Prior Publication Data

US 2013/0081170 P1 Mar. 28, 2013

Related U.S. Application Data

(60) Provisional application No. 61/540,305, filed on Sep. 28, 2011.

(30) Foreign Application Priority Data

Sep. 30, 2011 (NL) ..... PBR OPS852

(51) Int. Cl.
*A01H 5/00* (2006.01)
*A01H 5/02* (2006.01)

(52) U.S. Cl.
CPC ..... *A01H 5/02* (2013.01)
USPC ..... Plt./311

(58) Field of Classification Search
USPC ..... Plt./311
See application file for complete search history.

(56) References Cited

U.S. PATENT DOCUMENTS

| | | | | |
|---|---|---|---|---|
| PP10,394 P * | 5/1998 | Plate | ..... | Plt./311 |
| PP23,700 P3 * | 7/2013 | Schoone | ..... | Plt./311 |
| PP23,788 P3 * | 7/2013 | Schoone | ..... | Plt./311 |

* cited by examiner

*Primary Examiner* — Susan McCormick Ewoldt
(74) *Attorney, Agent, or Firm* — Foley & Lardner LLP; Sunit Talapatra

(57) ABSTRACT

A new and distinct *Phalaenopsis* plant named 'Deep Lake' particularly characterized by flowers which are white with purple spots and a purple mark in the center; the labellum is yellow with white and some purple; plants which may be propagated economically and uniformly using tissue culture; plants which produce more than one inflorescence; long and sturdy inflorescences; and relatively short, dark-green foliage.

3 Drawing Sheets

Latin name of the genus and species of the plant claimed: *Phalaenopsis* hybrid.

Variety denomination: 'Deep Lake'.

BACKGROUND OF THE INVENTION

The present invention relates to a new and distinct cultivar of *Phalaenopsis* plant, botanically known as *Phalaenopsis* of the Orchidaceae family, and hereinafter referred to by the cultivar name 'Deep Lake'.

*Phalaenopsis* comprises a genus of about 55 species of herbaceous perennials many of which, or the hybrids thereof, are suitable for cultivation in the home or greenhouse. *Phalaenopsis* is predominantly epiphytic or rock-dwelling, and is native to tropical Asia, the Malay Archipelago, and Oceania. The species typically has 2-ranked, fleshy, oblong or elliptic leaves affixed to a short central stem (monopodial growth), which vary in size from 5 to 8 inches to over 2 feet. The leaves may be entirely green or mottled with silver grey.

*Phalaenopsis* orchids, often referred to as 'Moth Orchids' in the horticultural trade, are frequently used to furnish cut flowers for the florist trade or sold as flowering potted-plants for home or interiorscape.

*Phalaenopsis* produces upright or pendent lateral racemes, often with many showy flowers which open in succession beginning with the lowermost. The flowers possess three sepals and three petals; the lateral ones being alike. The lowermost petal, called the labellum, is three-lobed and is often more brightly-colored than the other flower segments. Flower colors include various shades of pink, white, yellow and red-brown.

*Phalaenopsis* orchids are typically propagated from seeds. Asexual propagation of *Phalaenopsis* is often done from off-shoots which frequently arise from the lower bracts of the inflorescence. The resulting plants are detached from the mother plant and may be planted in a suitable substrate.

The new *Phalaenopsis* 'Deep Lake' is a product of a controlled breeding program conducted by the inventors, Rene Schoone, in Strengweg, Heemskerk, The Netherlands. The objective of the breeding program was to develop a new *Phalaenopsis* cultivar particularly characterized by its attractive and unique colored flowers, economical propagation via tissue culture, rapid growth, and a plant dimension suitable for packaging and shipping to the market.

The new *Phalaenopsis* 'Deep Lake' originated from a cross made by the inventor in 1999 in Strengweg, Heemskerk, The Netherlands. The female or seed parent is the *Phalaenopsis* cultivar designated 'Wonder Mountain', unpatented. The male or pollen parent is the *Phalaenopsis* cultivar designated 'Ching Hua Spring', unpatented. The new *Phalaenopsis* 'Deep Lake' was discovered and selected by the inventor as a single flowering plant within the progeny of the stated cross in a controlled environment in 2006 in Strengweg, Heemskerk, The Netherlands.

Asexual reproduction of the new *Phalaenopsis* cultivar by tissue culture was first performed in July, 2007 in Cieweg 13, Heemskerk, The Netherlands, and has demonstrated that the combination of characteristics as herein disclosed for the new cultivar are firmly fixed and retained through successive generations of asexual reproduction. The new cultivar asexually reproduces true-to-type.

BRIEF DESCRIPTION OF THE INVENTION

The following traits have been repeatedly observed and are determined to be unique characteristics of 'Deep Lake', which in combination distinguish this *Phalaenopsis* as a new and distinct cultivar:

1. flowers which are white with purple spots and a purple mark in the center; the labellum is yellow with white and some purple;
2. plant produces more than one inflorescence;
3. plants may be propagated economically and uniformly using tissue culture;
4. inflorescences are long and sturdy; and
5. relatively short, dark-green foliage.

In comparison with the parental cultivars of 'Deep Lake', the female parent 'Wonder Mountain' has white colored flowers with some yellow in the labellum. The flowers are about 11 cm in size. The male parent 'Ching Hua Spring' has white colored flowers with purple marks and a purple labellum. The flowers are about 8 cm in size. The flowers of 'Deep Lake' are white with purple spots and at the base a purple mark and some yellow, white and purple in the labellum. The flowers are about 8.5 to 9 cm in size.

Presently, the commercial cultivar to which 'Deep Lake' can be meaningfully compared is 'Bravery' (U.S. patent application Ser. No. 13/573,579). The flowers of 'Bravery' have more purple spots on the petals and sepals which are little darker in color than the spots of 'Deep Lake'. 'Bravery' has green/yellow in the labellum, whereas 'Deep Lake' has yellow in the labellum. Also the shape of the petals and sepals of 'Bravery' is rounder than the shape of the petals and sepals of 'Deep Lake'.

BRIEF DESCRIPTION OF THE PHOTOGRAPHS

The accompanying photographs illustrate the overall appearance of the new *Phalaenopsis* 'Deep Lake' showing the colors as true as is reasonably possible with colored reproductions of this type. Colors in the photographs may differ slightly from the color values cited in the detailed botanical description, which accurately describe the color of 'Deep Lake'.

DETAILED BOTANICAL DESCRIPTION

Figure 1:
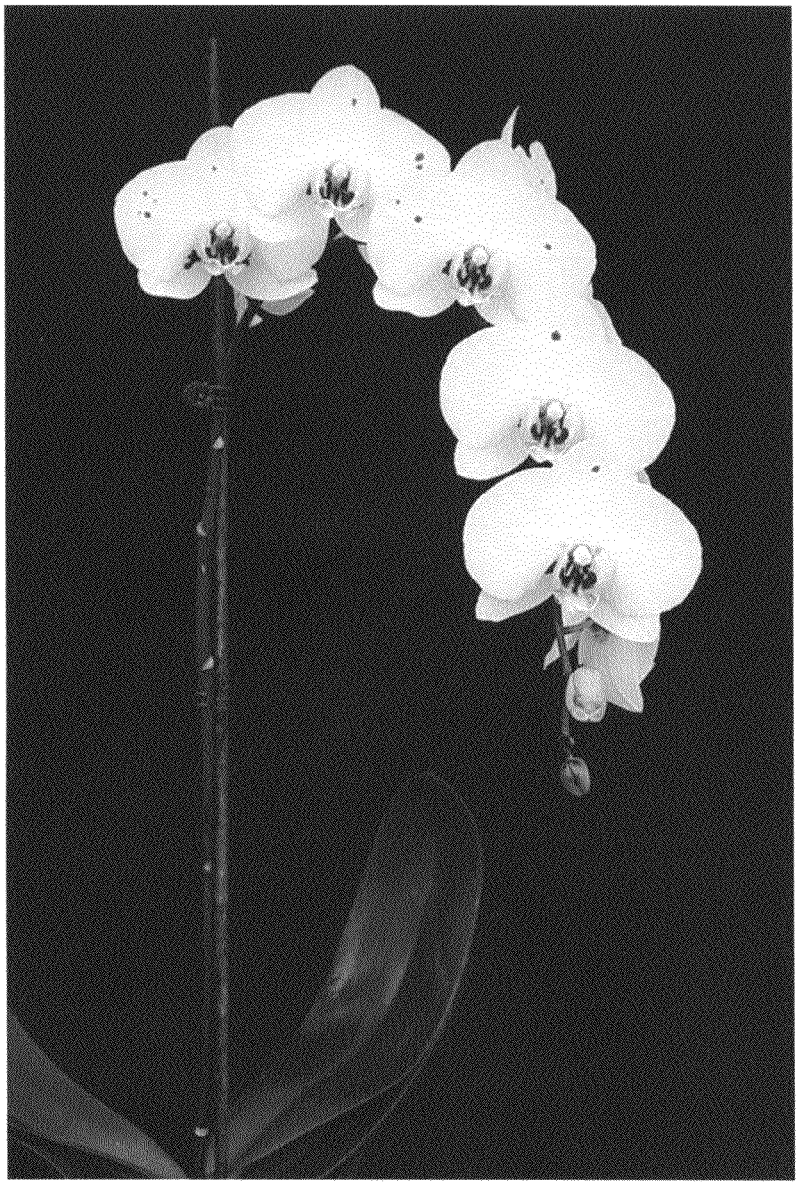
FIG. 1 shows a side view perspective of a typical flowering plant of 'Deep Lake' in a 12 cm pot, at 16 months of age.

The new *Phalaenopsis* cultivar 'Deep Lake' has not been observed under all possible environmental conditions. The phenotype of the new cultivar may vary with variations in environment such as temperature, light intensity, and day length without any change in the genotype of the plant.

The aforementioned photographs, together with the following observations, measurements and values describe plants of 'Deep Lake' as grown in a greenhouse in Strengweg, Heemskerk, The Netherlands, under conditions which closely approximate those generally used in commercial practice. Initially, the ideal temperature to grow plants of 'Deep Lake' is 27° C. during the day and at night. Then, during the flowering phase of 'Deep Lake', the ideal growing temperature is 20-22° C. during the day and 18° C. at night. Light levels for growing 'Deep Lake' are a minimum of 5,000 lux and a maximum of 10,000 lux. A balanced fertilizer with level of 200 ppm N, 87 ppm P, 168 ppm K is applied. Duration of growth of 'Deep Lake' from potting size is between 10 and 14 months.

Color references are made to The Royal Horticultural Society Colour Chart (R.H.S.), 2007 edition, except where general colors of ordinary significance are used. Color values were taken under daylight conditions at approximately noon in Zaandammerweg, Assendelft, The Netherlands. The age of the 'Deep Lake' plants described is 12 months after potting.

Classification:

*Botanical.*—*Phalaenopsis* hybrid.

Parentage:

*Female or seed parent.*—*Phalaenopsis* cultivar designated 'Wonder Mountain', unpatented.

*Male or pollen parent.*—*Phalaenopsis* cultivar designated 'Ching Hua Spring', unpatented.

Propagation:

*Type.*—Tissue culture.

*Rooting habit and description.*—Fleshy; approximately 4 mm-7 mm wide and green in color (RHS 137A); freely branching. It takes 12 weeks for plants growing in tissue culture to initiate roots.

Plant:

*Size at maturity.*—Height (from bottom of pot to highest flower): about 58 to 70 cm. Spread: about 35 to 60 cm.

*Growth habit.*—Large; green (RHS N137A) leaves and normal raceme.

*Vigor.*—Moderate.

*Crop time.*—Following asexual propagation, at about 26 weeks 2 leaves appear; at about 30 weeks 3-4 leaves appear; after a cold treatment of about 4-8 weeks at a temperature of about 19° C. about 2 racemes with flowers appear.

Foliage:

*Quantity per plant.*—About 6 to 8 leaves are produced before flowering.

*Arrangement and attachment.*—Half up/horizontal and on two sides.

*Overall shape of leaf.*—Oval, tip is blunt and asymmetric.

*Texture* (*both surfaces*).—Smooth and leathery.

*Pubescence.*—None.

*Leaf base.*—Acute.

*Margin.*—Entire.

*Mature leaf length.*—About 17 to 23 cm.

*Mature leaf width.*—About 8 to 12 cm.

*Mature leaf thickness.*—About 1 mm.

*Mature leaf color* (*upper surface*).—Green (RHS N137A).

*Mature leaf color* (*under surface*).—Green (RHS 137C).

*Venation.*—Pattern: parallel. Color of mid vein: upper surface: green (RHS N137A); under surface: green (RHS 137B).

Raceme:

*Quantity per plant.*—About 1 to 2.

*Number of flowers per raceme.*—About 7 to 12.

*Length.*—About 70 to 78 cm.

*Diameter.*—About 5 mm.

*Strength*.—Strong.

*Aspect*.—Upright.

*Texture*.—Glabrous and smooth.

*Color*.—Yellow/green (RHS 147A).

*Internode*.—Length: about 35 to 45 mm.

Inflorescence description:

*Appearance*.—upright to slightly pendant, racemose inflorescence with bilaterally symmetrical flowers that open in succession beginning with the lowermost flower.

*Buds*.—Height (from base to tip): about 25 to 29 mm. Diameter (at midpoint): about 21 to 25 mm. Shape: egg-shaped. Color: Main color is green/yellow (RHS 145B), at the base green/yellow (RHS 148B) and veins are purple (RHS N77C).

*Flowering time*.—For an untreated plant (flowering plant that has not undergone cold-treatment where the plant grows at a temperature of 18° C. to 19° C. for about 4 to 8 weeks after a period of about 30 weeks at a temperature of 25° C.), 2 racemes appear with about 16 to 20 flower buds and flowers per inflorescence. First flowers can be expected approximately 4 to 6 months after planting a plant with a leaf diameter of 3 to 5 cm. Flowers persistent.

*Flowering longevity*.—On the plant: about 4 to 6 months; lastingness of cut flowers: has not been observed.

*Fragrance*.—No fragrance.

Figure 2:
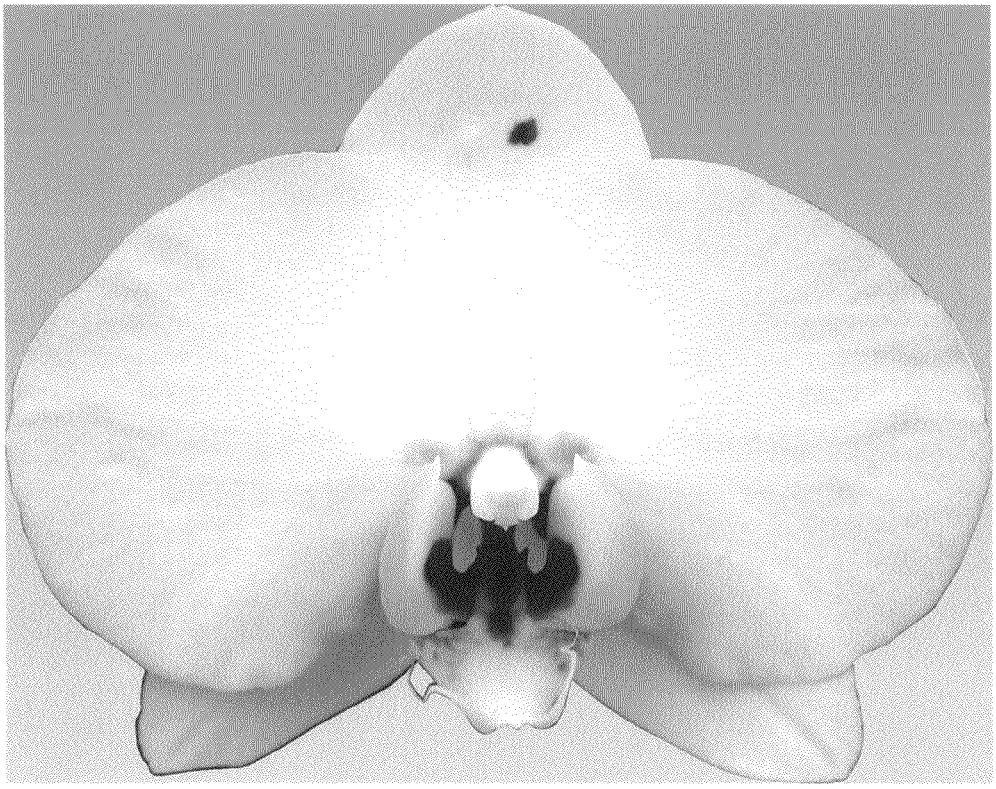
FIG. 2 shows a close-up view of a typical flower of 'Deep Lake'.
Figure 3:
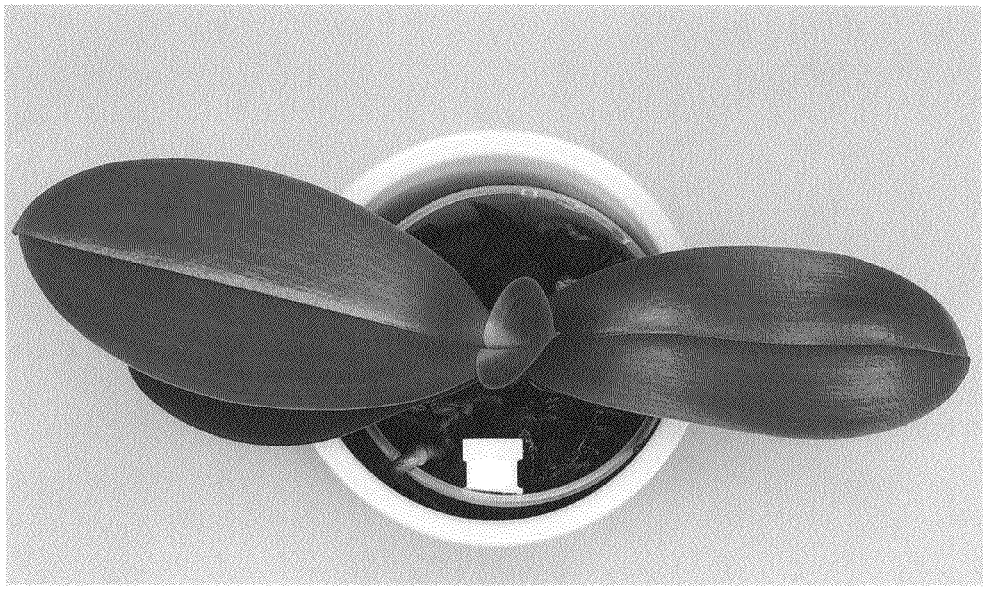
FIG. 3 shows a close-up view of the typical leaves of 'Deep Lake'

*Flower*.—Rate of opening: Flowers fully opened about 2 to 3 days after petal and sepal separation. Orientation at opening: slanted upward and outward. Shape: Typical shape of Phalaenopsis orchid; see FIG. 2 Size: Height: about 70 mm. Diameter: about 85 mm. Depth of tube: about 15 mm.

*Petals*.—Quantity and arrangement: three petals and three sepals that are trimerous, overlapping and arranged in 2 whorls. Petals are more pronounced than sepals. Arrangement: Inner whorl comprises 3 petals: 2 lateral petals and labellum. 2 lateral petals: Overall shape: broadly ovate and weakly cupped. Apex: oval. Margin: entire and weakly undulate. Base: broadly ovate. Length: about 55 mm. Width: about 40 mm. Texture: Upper surface: smooth and satiny. Under surface: smooth and satiny. Color (when fully opened): upper surface: Main color is white (RHS NN155C), at the base purple mark (RHS N79D) and some spots (RHS N79 B & N79C). Under surface: Main color is white (RHS NN155C with a yellow/green haze (RHS 145D). Labellum: Overall shape: 3-lobed with 2 prominent callosities at central junction of the lateral lobes and base of the midlobe. Lateral lobes of labellum fold upward about the column; the midlobe extends forward and is terminated by 2 filiform appendages at the apex. Lateral lobes of the labellum are ovate in shape while the midlobe is triangular with a bump and a rib on it. Margin: entire and weakly undulate. Length: about 19 mm. Width (not flattened): about 19 mm. Texture: Upper surface: smooth and satiny. Color (when fully opened): Mid lobe is yellow (RHS 7B) which turns into white (RHS NN155C). At the base the edge and spots are purple (RHS N79C). Under surface is yellow at the base (RHS 8D) which turns into white (RHS NN155C) and on the upper sides RHS 7B. Lateral lobes are white (RHS NN155C), at the base a purple mark (RHS N79C). The lower edge is yellow (RHS 7A). Under surface: main color is white (RHS NN155C) with on exterior some yellow (RHS 7A). Cirrhi: long. Color: main color is yellow (RHS 7B), rest is white (RHS NN155C). Pestle (Callosities): Length: About 8 mm. Width (not flattened): about 5 mm. Color: White (RHS NN155c) at the underside, on the front, back and top purple (RHS N79A) and an edge on the sides and on the front yellow (RHS 7B).

*Sepals*.—Arrangement: Outer whorl comprises 3 sepals. Overall shape: elliptical and weakly cupped. Margin: entire and weakly undulate. Length: about 40 to 50 mm. Width: about 25 to 39 mm. Apex: oval; little pointy. Texture: Upper & under surface: smooth and satiny. Color (when fully opened): Dorsal, upper surface: main color is white (RHS NN155C), spots are purple (N79C & N79B). Under surface: at the base yellow/green (RHS 145C) which turns into purple (RHS 76B) and white edges (RHS NN155C). Lateral, upper surface: Main color is white (RHS NN155C), at the base purple spots (RHS N79A) and yellow/green haze (RHS 145D). Under surface: main color yellow/green (RHS 145C), a purple haze (RHS 84C) and purple veins (RHS 84B).

*Pedicel*.—Length: 39 mm. Diameter: about 3 to 4 mm. Texture: glabrous and smooth. Color: yellow/green (RHS 144A) which turns into red/ purple (RHS N74C).

Reproductive organs:

*Arrangement*.—The stamens, style and stigmas are fused into a single, short structure called the column, possessing one terminal anther with pollen grains united into a pollinia, which are covered by an anther cap. The stigma is located under the column behind the pollinia. The ovary is inferior with three carpels present. The plant has not produced seed.

*Column*.—Length: about 7 mm. Diameter: about 6 mm. Color: white (RHS NN155C).

*Pollinia*.—Quantity: Two. Size: about 1 mm. Color: yellow/orange (RHS 23A).

*Ovary*.—Length: about 3 mm. Diameter: about 5 mm. Color: white (RHS N155C).

Disease/pest resistance/susceptibility: No specific resistance or susceptibility observed.

Temperature tolerance: Tolerant to a low temperature of about 15° C. and to a high temperature about 30° C.

What is claimed is:

1. A new and distinct *Phalaenopsis* plant named 'Deep Lake', as illustrated and described herein.

* * * * *